United States Patent [19]
Abe et al.

[11] Patent Number: 5,250,965
[45] Date of Patent: Oct. 5, 1993

[54] EYEBALL MICROSCOPE HAVING PARALLEL SLITS MOVING ACROSS THE OPTICAL PATH

[75] Inventors: Kuniomi Abe; Susumu Fujita, both of Kobe, Japan

[73] Assignee: Konan Camera Research Institute Inc., Hyogo, Japan

[21] Appl. No.: 769,787

[22] Filed: Oct. 2, 1991

[30] Foreign Application Priority Data

Oct. 25, 1990 [JP] Japan .............................. 2-112498[U]

[51] Int. Cl.$^5$ ................................................ A61B 3/10
[52] U.S. Cl. ..................................... 351/221; 351/205; 351/214; 359/368
[58] Field of Search ............... 351/221, 206, 233, 234, 351/214, 216, 205; 359/235, 285, 268, 900, 227, 232, 234, 235, 236, 368

[56] References Cited
U.S. PATENT DOCUMENTS 5,099,363  3/1992  Lichtman ............................ 359/385

FOREIGN PATENT DOCUMENTS 63-50010  10/1988  Japan .

Primary Examiner—Bruce Y. Arnold
Assistant Examiner—Hung Xuan Dang
Attorney, Agent, or Firm—Wegner, Cantor, Mueller & Player

[57] ABSTRACT

An eyeball microscope used for observing or photographing epitherial and endothelial cells and likes of a cornea, which is provided with an illuminating optical system for projecting an illuminating light beam onto an object, an observing optical system for observing or photographing an imaging light beam from the object and parallel slits moving across the optical paths of both optical systems, and arranged to scan the object with optical images of certain slits and, at the same time, to lead the imaging beam from the object through the same number of separate slits into the observing optical system, thereby shutting off all unwanted reflecting beams other than the imaging beam.

4 Claims, 3 Drawing Sheets

EYEBALL MICROSCOPE HAVING PARALLEL SLITS MOVING ACROSS THE OPTICAL PATH

BACKGROUND OF THE INVENTION

This invention relates to an eyeball microscope and, especially, to such microscope which enables clear observation of epithelial, intermedial and endothelial layers and likes of a cornea in a large field of view.

As shown in FIG. 1, in case of observing an endothelial cell layer 3 of a cornea 2, it had been a general practice in the prior art to illuminate the layer 3 with an illuminating light beam L which was projected through one half of an objective lens of a microscope and observe its imaging beam I through the other half of the objective lens. In this case, however, it was only a small portion W of a microscope field of view D that good observation was obtainable therein, since the imaging beam I of the endothelial cell layer 3 was very low in contrast and, moreover, obstructed by a strong reflecting beam R produced at a corneal surface 4.

In order to remove this disadvantage, an improvement has been proposed by such an invention as disclosed by Japanese patent publication No. S63-50010. According to this invention, as shown in FIG. 2, a narrow domain d of the endothelial cell layer 3 of the cornea 2 is illuminated by an illuminating beam 52 which has passed a certain slit 51a of a light shielding rotary member 51 having slits 51a, 51b, . . . formed therein, and an imaging beam 55 of the domain d is observed through another slit 51b of the rotary member 51. When the rotary member 51 is moved downwards in an arrow direction as shown, the observed domain d moves downwards in the microscope field of view D. Once such observation of the whole field of view D is completed, the uppermost portion of the field of view D is illuminated through the slit 51b, its imaging beam is observed through a succeeding slit 51c (not shown) and the observed domain moves similarly downwards. Accordingly, if the rotary member 15 is rotated at high speed in the arrow direction, the whole field of view can be observed as shutting off a reflecting beam 56 from the surface 4 of the cornea 2.

However, the invention of FIG. 2 has such a disadvantage in that the observed image is significantly dark as compared with the observable domain W according to the prior art system of FIG. 1, since the field of view is scanned from one end to the other end by a narrow observed domain d as in the case of television image scanned vertically from the top to the bottom by a horizontal scanning line. Since the contrast of the image of cornea endothelial cells is very low, such a dark image is very difficult to be focused in a microscope and may result in a trouble in observing or photographing the image.

Summary Of The Invention

Accordingly, an object of this invention is to remove the above-mentioned disadvantage of the prior art and provide an improved eyeball microscope which enables observation of a brighter image.

According to this invention, there is provided an eyeball microscope comprising a first lens to be positioned close to an object or eyeball, second and third lenses located in the rear of respective halves of the first lens, a first light shielding rotary member located in a conjugate focal plane of the object attributable to the first and second lenses, and a second light shielding rotary member located in a conjugate focal plane of the object attributable to the first and third lenses. Both rotary members have a plurality of substantially parallel slits formed therein at equal intervals. An illuminating optical system is located in the rear of the first rotary member for illuminating the object through the slits of the first rotary member and an observing optical system is located in the rear of the second rotary member for observing or photographing an imaging beam from the slits of the second rotary member. The first and second rotary members are rotationally driven in synchronism with each other so that the domain of the object which is illuminated through each slit of the first rotary member and the domain of the object which is observed through each slit of the second rotary member coincide always with each other.

The first and second rotary members and a driving device therefor may be included in a single unit which is detachable from a main body of the microscope which includes the remaining components.

These and other features of this invention will be described in more detail below in connection with a preferred embodiment with reference to the accompanying drawings.

DESCRIPTION OF THE PREFERRED EMBODIMENT

Figure 3:
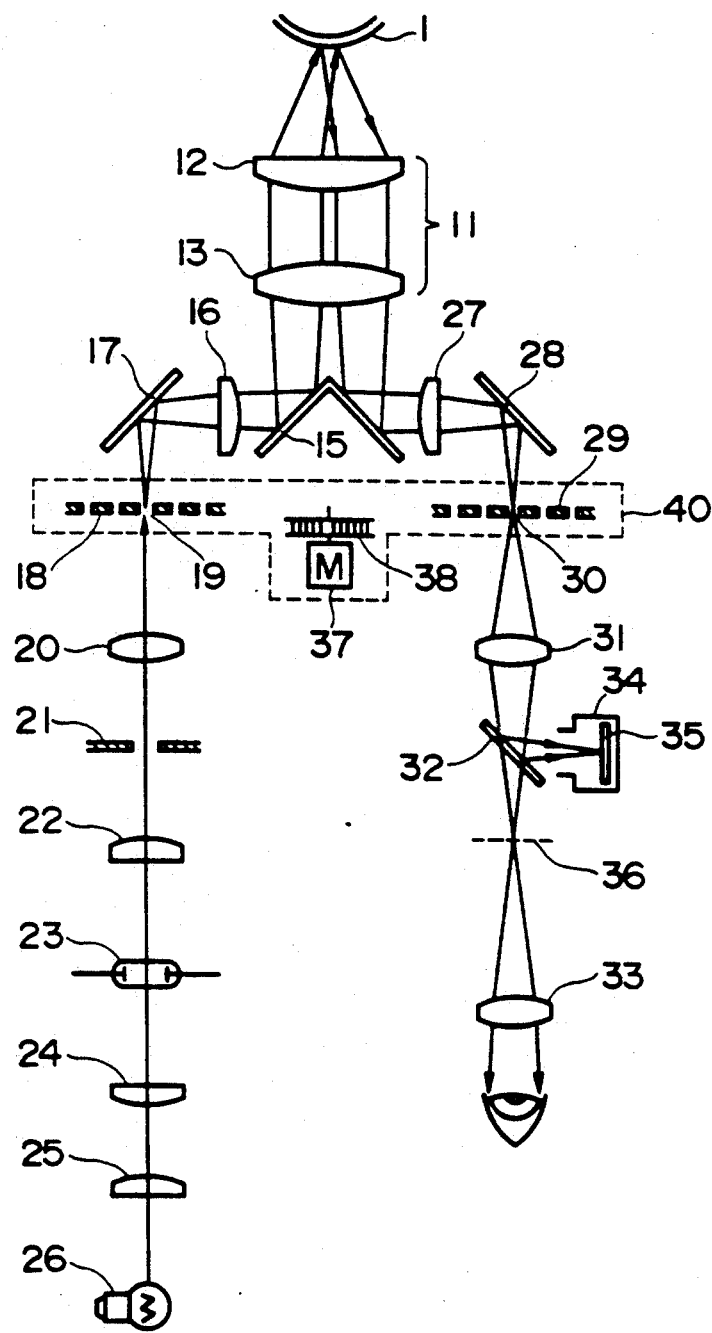
FIG. 3 is a schematic diagram showing a general configuration of an embodiment of the eyeball microscope according to this invention.

Referring to FIG. 3, a common objective lens 11 is composed of a fore lens 12 and a rear lens 13 and a parallel beam region is formed between the fore and rear lenses 12 and 13 for the purpose of preventing a focus of the microscope from changing with movement of the fore lens together with an eyeball 1. An angle mirror 15 is disposed behind the objective lens 11 for dividing an optical path into left and right halves as shown.

The left optical path from the mirror 15 passes a lens 16 and is folded normally again by a mirror 17 in a direction parallel to the optical axis of the objective lens 11 and, thereafter, it passes a slit 19 of a light shielding disc 18, a lens 20, an iris 21 and lens 22, a flash discharge tube 23 and condenser lenses 24 and 25 and reaches a lamp 26. An illuminating beam generated from the lamp 26 is focused by the condenser lenses 25 and 24 at the position of flash discharge tube 23 and again focused by the lens 22 at the position of iris 21 and it is further focused by the lenses 20 and 16 in the vicinity of an entrance pupil of the objective lens 11. The iris 21 has a semicircular opening for preventing random reflection of the illuminating beam colliding against a body tube of the objective lense 11. An image of the slit 19 is projected on the eyeball 1 by the lenses 16 and 11, so that the eyeball 1 is illuminated in a shape of the slit 19.

The right optical path from the mirror 15 passes a lens 27 and folded again by a mirror 28 in a direction parallel to the optical axis of the objective lens 11 and, thereafter, it passes a slit 30 of another light shielding disc 29, a lens 31 and a half mirror 32 and is observed through an eyepiece 33 and, at the same time, reflected by the half mirror 32 to reach a film 35 in a camera 34. A movable mirror may be used instead of the half mirror 32 to select the optical path for either the eyepiece 33 or the camera 34. Accordingly, an image of the eyeball 1 is formed at a position of the disc 29 by the lens 11, mirror 15, lens 27 and mirror 28 and this image is imaged again on a spatial plane 36 by the lens 31 through the slit 30 and then magnified by the eyepiece 33 for observation. The image on the disc 29 is also imaged again on the film 35 of the camera 34 by the lens 31 and half mirror 32.

Figure 1:
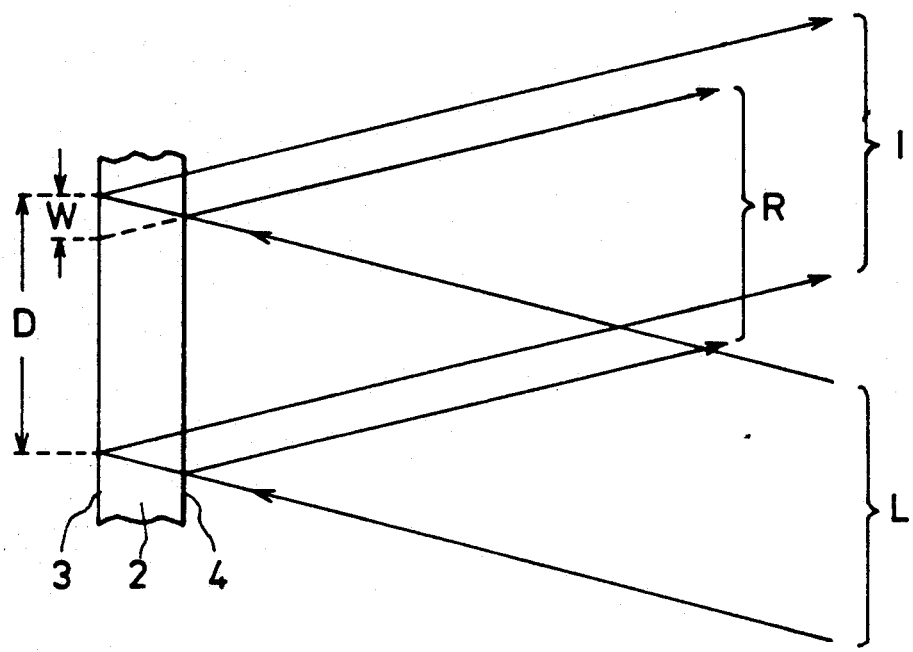
FIGS. 1 and 2 are explanatory diagrams showing mutual relationships of the illuminating, imaging and reflecting beams in the prior art eyeball microscopes.
Figure 2:
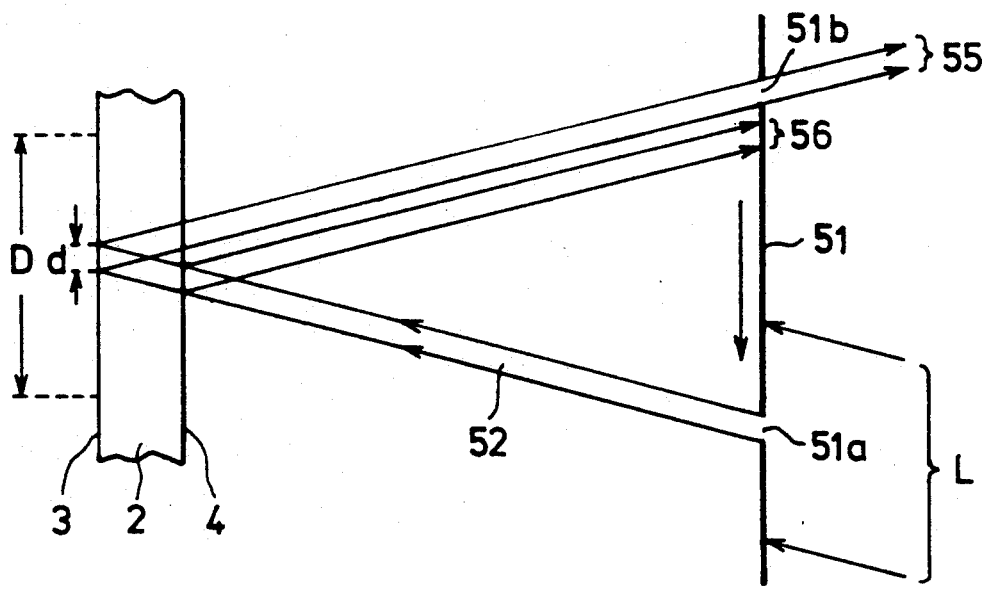
Figure 4:
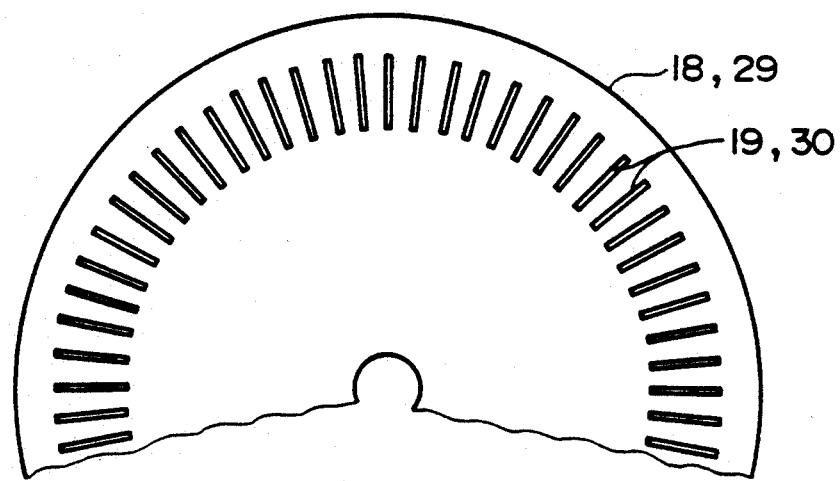
FIG. 4 is a front view showing a light shielding rotary member of the embodiment of FIG. 3.

The light shielding discs 18 and 29 are of the same design and have narrow radial slits 19 and 30, respectively, arranged at equal intervals, as shown in FIG. 4. The interval of the slits is much less than that of the prior art disc of FIG. 2. The discs 18 and 29 are rotationally driven at high speed by a motor 37 in synchronism with each other through a toothed pulley 38 and a toothed belt (not shown).

Figure 5:
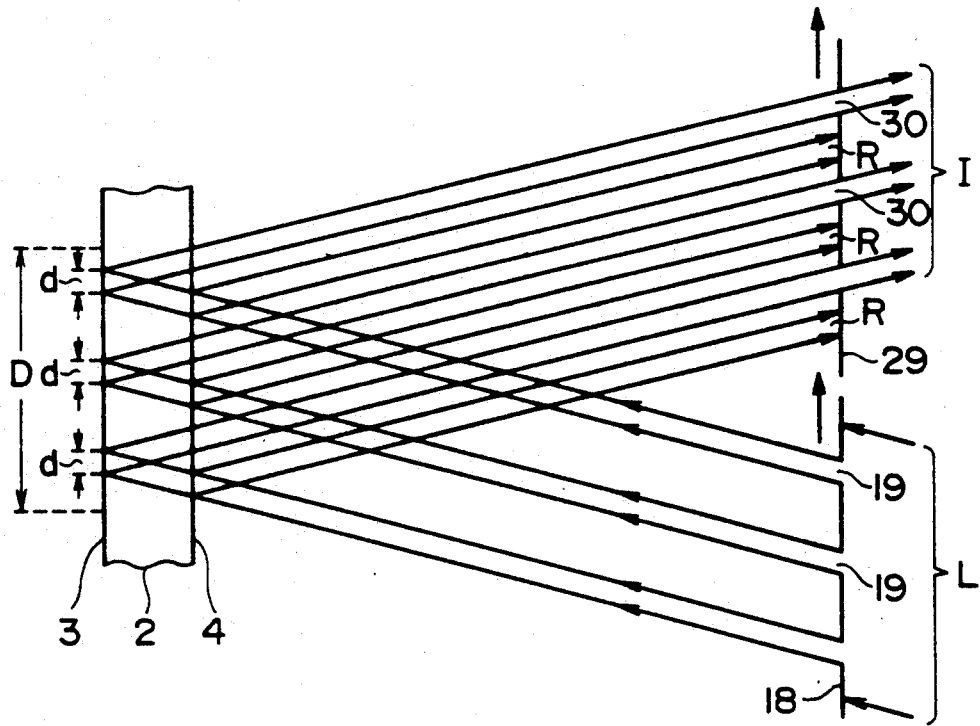
FIG. 5 is an explanatory diagram showing a mutual relationship of the illuminating, imaging and reflecting beams in the embodiment of FIG. 3.

As a result, in the case of observing the endothelial cell. layer 3 of the cornea 2, illuminating beams L having passed the slits 19 of the light shielding disc 18 illuminate the cornea 2 in the microscope field of view D in a pattern of stripes of a width d which are vertical to the plane of paper, as shown in FIG. 5. While imaging beams I are taken out through the slits of the light shielding disc 29, reflecting beams R produced by the cornea surface 4 are shut off by the disc 29 since they miss the slits 30. Since the light shielding discs 18 and 29 rotate in synchronism with each other and the slits 19 and 30 move in the arrow direction, the microscope field of view D of the endothelial cell layer 3 is successively scanned by the pattern of stripes of width d to enable onservation of the whole field of view without much obstruction of the reflecting beams R.

While the thickness of a cornea is about 0.5 millimeter in the case of mankind, it is only about 0.2 to 0.3 millimeter in the case of small animals for experiment. In order to accommodate with such variation of the cornea thickness, it is desirable to change the pitch or interval of the slits 19 and 30 of the light shielding discs 18 and 29. The embodiment of FIG. 3 may be arranged preferably to include the discs 18 and 29 and the driving motor 37 therefore in a single unit 40 as shown in phantom for changing the pitch of slits by exchanging this unit 40.

As described above, in accordance with this invention, it is possible to obtain a brighter image as compared with the prior art device in which the object is illuminated by a single illuminating beam in a pattern of single bar and the microscope field of view is scanned as taking out an imaging beam only from the illuminated domain, thereby facilitating focusing, observation and photographing of the microscope, since the object is illuminated concurrently by plural illuminating beams in a pattern of stripes and the field of view is scanned by these stripes as taking out the imaging beams therefrom. Moreover, the microscope can be accomodated to variation of the cornea thickness of the object by exchanging a compact unit as above-mentioned.

It should be noted that various modifications, variations and changes can be made on the above-mentioned embodiment without leaving the scope of this invention as defined in the appended claims. For example, the light shielding rotary members need not take a shape of circular disc as shown and may be of any other suitable shape. Moreover, it will be obvious that the use of separate light shielding rotary members for illumination and observation as in the above-mentioned embodiment has no direct connection to the object of this invention, and that the same effect can be obtained by using a single light shielding rotary body in common as in the prior art device shown in FIG. 2 and arranging to pass the illuminating and imaging beams concurrently through different plural slits, respectively.

We claim:

1. An eyeball microscope comprising:
   a first lens to be positioned close to an object;
   second and third lenses located rearwardly of respective halves of said first lens as viewed from said object;
   a first light shielding rotary member having substantially parallel slits arranged at equal intervals to traverse an optical axis of said second lens in a conjugate focal plane of said object attributable to said first and second lenses;
   a second light shielding rotary member having substantially parallel slits arranged at equal intervals to traverse an optical axis of said third lens in a conjugate focal plane of said object attributable to said first and third lenses;
   an illuminating optical system for projecting an illuminating light beam onto said object through the slits of said first light shielding rotary member to form images of said slits on said object;
   an observing optical system for observing or photographing an imaging light beam from said object through the slits of said second light shielding rotary member;
   a driving device for rotating said first and second light shielding rotary members in synchronism with each other to move said images of the slits normally thereto and lead the imaging light beams from said moving images into said observing optical system through the slits of said second light shielding rotary member;
   wherein the intervals of the slits of said light shielding rotary members are selected so that images of certain slits of said first light shielding rotary member are always projected onto said object and all of said images are concurrently observed or photographed through slits of said second light shielding rotary member which are same in number as said certain slits.

2. An eyeball microscope as set forth in claim 1 wherein said first and second light shielding rotary members and said driving device are included in a single unit which is detachable from a main body of said microscope.

3. An eyeball microscope comprising:
   a first lens to be positioned close to an object;
   second and third lenses located rearwardly of respective halves of said first lens as viewed from said object;
   a light shielding rotary member having substantially parallel slits arranged at equal intervals to traverse an optical axis of said second lens in a conjugate focal plane of said object attributable to said first and second lenses and, also, an optical axis of said third lens in a conjugate focal plane of said object attributable to said first and third lenses;

an illuminating optical system for projecting an illuminating light beam onto said object simultaneously through a plurality of certain slits of said light shielding rotary member to form a plurality of images, corresponding to said certain slits, on said object;

an observing optical system for observing or photographing an imaging light beam from said object simultaneously through a plurality of other slits of said light shielding rotary member;

a driving device for rotating said light shielding rotary member to move said plurality of images normally thereto;

wherein the intervals of the slits of said light shielding rotary members are selected so that plural images corresponding to said certain slits are simultaneously projected onto said object and all of said plural images are concurrently observed or photographed through said other slits which are same in number as said certain slits.

4. An eyeball microscope as set forth in claim 3 wherein said light shielding rotary member and said driving device are included in a single unit which is detachable from a main body of said microscope.

* * * * *